US010677698B2

(12) United States Patent
Reed

(10) Patent No.: US 10,677,698 B2
(45) Date of Patent: Jun. 9, 2020

(54) SYSTEM AND METHOD FOR MANUFACTURING CEMENTITIOUS BOARDS WITH ON-LINE SLURRY SET MEASUREMENT

(71) Applicant: United States Gypsum Company, Chicago, IL (US)

(72) Inventor: Paul W. Reed, Chicago, IL (US)

(73) Assignee: United States Gypsum Company, Chicago, IL (US)

( * ) Notice: Subject to any disclaimer, the term of this patent is extended or adjusted under 35 U.S.C. 154(b) by 0 days.

(21) Appl. No.: 15/183,173

(22) Filed: Jun. 15, 2016

(65) Prior Publication Data

US 2017/0363524 A1    Dec. 21, 2017

(51) Int. Cl.
| | | |
|---|---|---|
| *G01N 3/08* | (2006.01) | |
| *G01N 19/10* | (2006.01) | |
| *G01N 33/38* | (2006.01) | |
| *B28B 17/00* | (2006.01) | |
| *B28B 19/00* | (2006.01) | |

(52) U.S. Cl.
CPC ........... *G01N 3/08* (2013.01); *B28B 17/0072* (2013.01); *G01N 19/10* (2013.01); *G01N 33/383* (2013.01); *B28B 19/0092* (2013.01)

(58) Field of Classification Search
CPC ........ G01N 3/08; G01N 33/383; G01N 19/10; G05B 19/402; C04B 11/00; B29C 65/00; B28B 17/0072; B28B 19/0092
USPC .......................................................... 73/818
See application file for complete search history.

(56) References Cited

U.S. PATENT DOCUMENTS

| | | |
|---|---|---|
| 2,436,435 A | 2/1948 | Kent |
| 2,656,716 A | 10/1953 | Hoggatt |
| 2,834,202 A | 5/1958 | Cook |
| 2,834,203 A | 5/1958 | Sampson |
| 3,194,061 A | 7/1965 | Sorenson et al. |
| 3,822,588 A | 7/1974 | Knight et al. |
| 3,973,432 A | 8/1976 | Toulc'Hoat et al. |

(Continued)

OTHER PUBLICATIONS

European Patent Office, International Search Report and the Written Opinion in International Application No. PCT/US2017/036737 (dated Sep. 28, 2017).

*Primary Examiner* — Octavia Hollington
(74) *Attorney, Agent, or Firm* — Leydig, Voit & Mayer, Ltd.; Philip T. Petti; Pradip K. Sahu

(57) ABSTRACT

Embodiments of a system and a method for measuring cementitious board during its continuous manufacture can be used online in a continuous manufacturing process to effectively determine the degree to which cementitious slurry has set (e.g., expressed as percent hydration) at a predetermined location, such as, near a cutting station, for example. A compression assembly can be used to compressively engage the cementitious board in a controlled manner as it passes by the compression member along the conveyor between the forming station and the cutting station. A force gauge can be associated with the compression member to measure the resistance force exerted by the cementitious board in response to being compressed by the compression member. The resistance force can be correlated to a set characteristic of the cementitious board, such as a numerical value of percent hydration of the cementitious slurry of that particular portion of the cementitious board.

25 Claims, 5 Drawing Sheets

(56) References Cited

U.S. PATENT DOCUMENTS

| | | |
|---|---|---|
| 4,864,851 A | 9/1989 | Houghton |
| 4,866,984 A | 9/1989 | Houghton |
| 4,970,895 A | 11/1990 | Houghton et al. |
| 4,991,432 A | 2/1991 | Houghton et al. |
| 5,013,403 A | 5/1991 | Chase |
| 5,049,057 A | 9/1991 | Yamaguchi et al. |
| 5,101,661 A | 4/1992 | Cresson et al. |
| 5,138,878 A | 8/1992 | Cresson et al. |
| 6,125,685 A | 10/2000 | Collier et al. |
| 6,520,004 B1 | 2/2003 | Lin |
| 6,786,083 B1 | 9/2004 | Bain et al. |
| 7,104,031 B2 | 9/2006 | Baggot et al. |
| 7,204,154 B2 | 4/2007 | Sartain et al. |
| 7,223,311 B2 * | 5/2007 | Conboy ................. B28B 11/16 156/347 |
| 7,380,443 B2 | 6/2008 | Tsujii et al. |
| 7,387,015 B2 | 6/2008 | Chancellor et al. |
| 7,475,599 B2 * | 1/2009 | Frank ................... G01B 5/061 73/803 |
| 7,803,226 B2 | 9/2010 | Wang et al. |
| 7,811,685 B2 | 10/2010 | Wang et al. |
| 7,815,730 B2 | 10/2010 | Wang et al. |
| 7,987,730 B2 * | 8/2011 | Tackett ................. B29C 44/60 73/790 |
| 8,070,895 B2 | 12/2011 | Engbrecht et al. |
| 8,133,600 B2 | 3/2012 | Wang et al. |
| 8,312,764 B2 | 11/2012 | Valleggi et al. |
| 8,382,923 B2 * | 2/2013 | Okazaki ................. B28B 1/29 156/346 |
| 8,501,074 B2 | 8/2013 | Wang et al. |
| 8,568,544 B2 | 10/2013 | Engbrecht et al. |
| 8,651,481 B2 | 2/2014 | Woodford |
| 8,656,759 B2 | 2/2014 | Hughes et al. |
| 10,040,725 B2 * | 8/2018 | Perez-Pena ............ C04B 24/04 |
| 2005/0055975 A1 | 3/2005 | Tackett et al. |
| 2007/0022913 A1 | 2/2007 | Wang et al. |
| 2008/0190062 A1 | 8/2008 | Engbrecht et al. |
| 2009/0239087 A1 | 9/2009 | Wang et al. |
| 2010/0055477 A1 | 3/2010 | Wang et al. |
| 2011/0009564 A1 | 1/2011 | Wang et al. |
| 2011/0196090 A1 | 8/2011 | Wang et al. |
| 2012/0040168 A1 | 2/2012 | Engbrecht et al. |
| 2014/0041445 A1 | 2/2014 | Chun et al. |
| 2014/0224003 A1 | 8/2014 | Zhang et al. |
| 2015/0285722 A1 | 10/2015 | Wu et al. |

* cited by examiner

SYSTEM AND METHOD FOR MANUFACTURING CEMENTITIOUS BOARDS WITH ON-LINE SLURRY SET MEASUREMENT

BACKGROUND

The present disclosure relates to continuous cementitious board manufacturing processes and, more particularly, to a system and method for measuring the degree to which cementitious slurry has set at a predetermined point along the manufacturing line during its manufacture.

In many types of cementitious articles, set gypsum (calcium sulfate dihydrate) is often a major constituent. For example, set gypsum is a major component of end products created by use of traditional plasters (e.g., plaster-surfaced internal building walls), and also in faced gypsum board employed in typical drywall construction of interior walls and ceilings of buildings. In addition, set gypsum is the major component of gypsum/cellulose fiber composite boards and products, as described in U.S. Pat. No. 5,320,677, for example. Typically, such gypsum-containing cementitious products are made by preparing a mixture of calcined gypsum (calcium sulfate alpha or beta hemihydrate and/or calcium sulfate anhydrite), water, and other components, as appropriate to form cementitious slurry. The cementitious slurry and desired additives are often blended in a continuous mixer, as described in U.S. Pat. No. 3,359,146, for example.

In a typical cementitious board manufacturing process such as gypsum wallboard, cementitious board is produced by uniformly dispersing calcined gypsum (commonly referred to as "stucco") in water to form aqueous calcined gypsum slurry. The aqueous calcined gypsum slurry is typically produced in a continuous manner by inserting stucco and water and other additives into a mixer which contains means for agitating the contents to form a uniform gypsum slurry. The slurry is continuously directed toward and through a discharge outlet of the mixer and into a discharge conduit connected to the discharge outlet of the mixer. Aqueous foam can be combined with the aqueous calcined gypsum slurry in the mixer and/or in the discharge conduit. A stream of foamed slurry passes through the discharge conduit from which it is continuously deposited onto a moving web of cover sheet material (i.e., the face sheet) supported by a forming table. The foamed slurry is allowed to spread over the advancing face sheet. A second web of cover sheet material (i.e., the back sheet) is applied to cover the foamed slurry and form a sandwich structure of a continuous wallboard preform. The wallboard preform is subjected to forming, such as at a conventional forming station, to obtain a desired thickness.

The calcined gypsum reacts with the water in the wallboard preform to form a matrix of crystalline hydrated gypsum or calcium sulfate dihydrate and sets as a conveyor moves the wallboard preform down the manufacturing line. The hydration of the calcined gypsum provides for the formation of an interlocking matrix of set gypsum, thereby imparting strength to the gypsum structure in the gypsum-containing product. The product slurry becomes firm as the crystal matrix forms and holds the desired shape.

After the wallboard preform is cut into segments downstream of the forming station at a point along the line where the preform has set sufficiently, the segments are flipped over, dried (e.g., in a kiln) to drive off excess water, and processed to provide the final wallboard product of desired dimensions. The aqueous foam produces air voids in the set gypsum, thereby reducing the density of the finished product relative to a product made using a similar slurry but without foam.

In general, the hydration rate can impact the final strength and production speed of the gypsum-containing product. Furthermore, in the process for making cementitious boards, the setting and drying steps are the most intensive in terms of time and energy. The setting time of the slurry depends on a number of factors, including the age of the calcined gypsum, impurities in the calcined gypsum, surface area, pH, particle size, and the temperature at the time of mixing. Different additives and/or process condition changes can be employed to influence the hydration rate of the slurry to ensure that the cementitious board being produced is suitable for its intended purpose. Accordingly, it is desirable for an operator to determine the rate of set that the cementitious slurry undergoes as it progresses along the line.

Conventionally, an operator at a cutting station, which is located downstream of the forming station at a position where the slurry is expected to have sufficiently set so that the wallboard preform can be cut into segments, uses a "thumb test" to periodically monitor the hydration rate (or set time) of the slurry. The thumb test comprises pushing one's thumb on the back of the board to feel how firm it is. An operator must be in attendance to measure the hardness periodically by pressing the board with a thumb, and the operator decides by experience whether the board is sufficiently set. It can be difficult to compare data from thumb tests taken at different times and/or by different operators.

Also, it is known to monitor the temperature rise of the slurry as it sets. The temperature of the cementitious slurry rises during the setting process, which is an exothermic reaction that generates heat. The temperature of the slurry increases over time, eventually reaching a maximum temperature as the hydration reaction moves toward completion. A temperature rise set (TRS) curve can be plotted which tracks temperature over time so that an operator can determine a hydration percentage for the slurry at various points along the machine line. However, obtaining temperature rise set data on a continuous basis can be difficult, including overcoming difficulties caused by ambient temperature or other influences.

There is a continued need in the art to provide additional solutions to enhance the production of cementitious boards. For example, there is a continued need for techniques for monitoring the set of cementitious slurry during the manufacture of a cementitious board.

It will be appreciated that this background description has been created by the inventor to aid the reader and is not to be taken as an indication that any of the indicated problems were themselves appreciated in the art. While the described principles can, in some aspects and embodiments, alleviate the problems inherent in other systems, it will be appreciated that the scope of the protected innovation is defined by the attached claims and not by the ability of any disclosed feature to solve any specific problem noted herein.

SUMMARY

In one aspect, the present disclosure is directed to embodiments of a system for manufacturing a cementitious board. For example, in one embodiment, a system for manufacturing a cementitious board is disclosed in which the cementitious board has a cementitious core interposed between a pair of cover sheets. The cementitious core is formed from an aqueous cementitious slurry. The system for manufacturing includes a forming station, a conveyor, and a slurry set measurement system.

The forming station is configured to form the cementitious board such that the cementitious board is within a predetermined thickness range. The conveyor is configured to convey the cementitious board along a machine direction away from the forming station. The conveyor extends along the machine direction and a cross-machine direction. The cross-machine direction is perpendicular to the machine direction. The slurry set measurement system is configured to measure a set characteristic of the aqueous cementitious slurry of the cementitious board. The slurry set measurement system includes a compression member, an actuator assembly, and a force gauge.

The compression member is disposed over the conveyor at a measurement position which is in downstream relationship to the forming station along the machine direction. The actuator assembly is configured to selectively move the compression member over a range of travel along a normal axis between a stowed position and an engaged position. The normal axis is substantially perpendicular to the machine direction and to the cross-machine direction. The engaged position is configured to place the compression member in contacting relationship with the cementitious board supported by the conveyor such that the compression member exerts pressure against the cementitious board.

The force gauge is associated with the compression member such that the force gauge is configured to measure a resistance force against the compression member along the normal axis in response to the compression member being in contacting relationship with the cementitious board. The force gauge is configured to generate a force signal indicative of the resistance force.

In another aspect of the present disclosure, embodiments of a method of manufacturing a cementitious board are described. For example, in one embodiment, a method of manufacturing a cementitious board includes conveying the cementitious board along a machine direction away from a forming station. The cementitious board has a cementitious core interposed between a pair of cover sheets. The cementitious core comprises an aqueous cementitious slurry. The cementitious board extends along the machine direction and along a cross-machine direction which is perpendicular to the machine direction.

A portion of the cementitious board is compressed by positioning a compression member along a normal axis such that the compression member is in engaging contact with the portion of the cementitious board. The normal axis is substantially perpendicular to the machine direction and to the cross-machine direction. The compression member is disposed at a measurement position in downstream relationship to the forming station along the machine direction.

A resistance force, which is exerted by the portion of the cementitious board against the compression member in response to the compression member being in engaging contact with the portion of the cementitious board, is measured. A force signal is transmitted to a processor. The force signal is indicative of the measured resistance force. A slurry set measurement program stored upon a non-transitory computer-readable medium is executed using the processor to display a value for a set characteristic of the aqueous cementitious slurry of the portion of the cementitious board based upon the force signal. The value is displayed through a graphical user interface using a display device operably arranged with the processor.

Further and alternative aspects and features of the disclosed principles will be appreciated from the following detailed description and the accompanying drawings. As will be appreciated, the systems and techniques for measuring the degree to which cementitious slurry has set during the manufacture of a cementitious article that are disclosed herein are capable of being carried out and used in other and different embodiments, and capable of being modified in various respects. Accordingly, it is to be understood that both the foregoing general description and the following detailed description are exemplary and explanatory only and do not restrict the scope of the appended claims.

Figure 1:
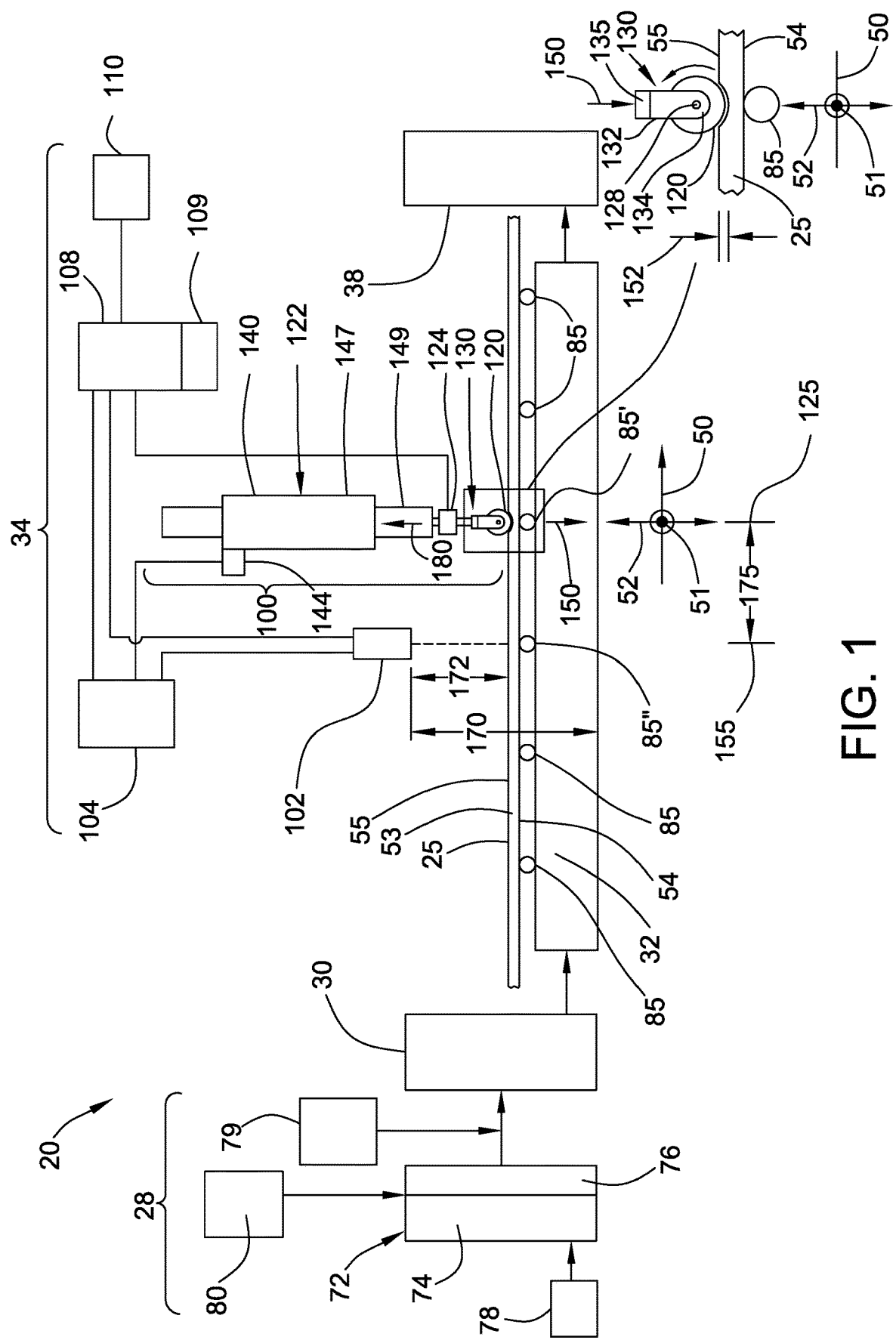
FIG. 1 is a fragmentary, schematic side elevational view of an embodiment of a system for manufacturing a cementitious board made from an aqueous cementitious slurry in the form of a gypsum wallboard manufacturing line which is constructed in accordance with principles of the present disclosure, the system including an embodiment of a system for measuring set in the aqueous cementitious slurry which is constructed in accordance with principles of the present disclosure and is positioned at a predetermined location along the manufacturing line.

It should be understood that the drawings are not necessarily to scale and that the disclosed embodiments are sometimes illustrated diagrammatically and in partial views. In certain instances, details which are not necessary for an understanding of this disclosure or which render other details difficult to perceive may have been omitted. It should be understood that this disclosure is not limited to the particular embodiments illustrated herein.

DETAILED DESCRIPTION OF EXEMPLARY EMBODIMENTS

The present disclosure provides various embodiments of a system and a method for manufacturing cementitious board having means for measuring the set of the aqueous cementitious slurry forming the core of the cementitious board during the board's continuous manufacture that can be used in connection with the manufacture of various cementitious products, including gypsum wallboard, for example. Embodiments following principles of the present disclosure of a system and a method for measuring cementitious slurry set during the continuous manufacture of cementitious board can be used online in a continuous manufacturing process to effectively determine the degree to which cementitious slurry has set (e.g., expressed as percent hydration) at a predetermined location, such as, near a cutting station, for example. In embodiments, the system can be configured to issue an operator alert when a target percent hydration range is not satisfied.

In embodiments following principles of the present disclosure, a system for measuring set in aqueous cementitious slurry of a cementitious board as the board is being manufactured can be configured as an automatic system for measuring percent hydration (or a correlated characteristic indicative of set) during the production of the cementitious board (e.g., gypsum wallboard) at a point in the production process before it is dried (e.g., in a kiln). In embodiments, the system includes a support frame extending over a conveyor that leads to a rotary cut-off knife. A compression member, which in embodiments can be in the form of an undriven roller (e.g., a wheel), can be associated with a compression-type load cell or other force measuring device or gauge. The force gauge, in turn, is suspended from an actuator assembly (e.g., a linear actuator) configured to selectively raise and lower the load cell and wheel assembly to contact the cementitious board being carried along by the conveyor to the cut-off knife and apply a predetermined force to the compression member. The actuator assembly can be configured to lower the compression wheel to engage the cementitious board and apply a compressive load to move the compression member downwardly into the cementitious board a predetermined compression distance (e.g., up to approximately $\frac{1}{16}$" into the board). In embodiments where the compression member comprises a roller, the roller can rotate in response to the relative movement of the cementitious board with which it is in contact along the machine direction as it is carried by the conveyor past the compression member to the cut-off knife.

The force gauge can be configured to measure the resistance force exerted by the cementitious board against the compression member in response to the compression member being driven into the board by the actuator assembly. The resistance force is correlated to the compressive strength of the cementitious board as a result of the degree to which the aqueous cementitious slurry in the cementitious board has set at that point. The measured resistance force is also proportional to the percent hydration of the aqueous cementitious slurry in the cementitious board at that point.

In embodiments, the resistance force data are transmitted to a processor. A slurry set measurement program stored upon a non-transitory computer-readable medium is executed using the processor to generate a numerical value relating to a board set characteristic based upon the resistance force generated by a particular portion of the cementitious board in response to being compressed the compression distance by the compression member. In embodiments, the slurry set measurement program is configured to determine a value of percent hydration of the aqueous cementitious slurry of a particular portion of the cementitious board based upon the resistance force measured for the particular portion of the cementitious board.

The measurement of the set characteristic of the aqueous cementitious slurry of the board can be based on the measurement of hardness by the penetration of the compression member (which has an external contact surface with a fixed size). The resistance force generated in response to compressing the cementitious board is a measure of its hardness. Use of the measured resistance force by the processor, which is specially programmed with a slurry set measurement program, can be used rather than relying upon manual testing in determining the set of the cementitious board. The measured resistance force can be used by the processor to determine accurate set characteristic data for the cementitious board in an online manner as it is in being manufactured.

In embodiments, the compression assembly can be automatically rotated out of the way in order to allow thick startup material to pass underneath. In use, the unit can be rotated into position so that the compression member is proximate to the cementitious board to be tested (e.g., approximately 1½" above the cementitious board).

Embodiments of a system for measuring set in aqueous cementitious slurry of a cementitious board following principles of the present disclosure can be useful to automatically measure the percent hydration and hardness of the setting slurry in the cementitious board during its production and before it is cut into segments. In embodiments, the measurement of slurry set can be performed automatically and be fed as an input to a process control computer to identify when the cementitious board is hard enough to cut (e.g., at start up of the line) and when the cementitious board becomes too soft (e.g., through periodic set measurement during production runs). Embodiments of a system for measuring set in aqueous cementitious slurry of a cementitious board following principles of the present disclosure can be used to carry out a method of measuring set of aqueous cementitious slurry in cementitious board as it is being made can be used to automatically measure board set without the need to use a human operator to manually perform the test, helping to reduce operator intervention and labor. The system can be used to directly measure cementitious board hardness and transmit the measured value electronically to a control computer for automated monitoring and response when threshold limits are not satisfied. In embodiments, the values for cementitious slurry set generated using principles of the present disclosure can be used to help a line operator control the quality of the board being made and/or help control the quality of the cut made at the cutting station.

Turning now to the Figures, an embodiment of a system 20 for manufacturing a cementitious board 25 constructed according to principles of the present disclosure is shown in FIG. 1. The illustrated system 20 includes a wet end system 28, a forming station 30, a conveyor 32, a slurry set measurement system 34, and a cutting station 38.

The wet end system 28 and the forming station 30 are configured to mix and assemble constituent materials together such that a continuous cementitious board 25 having a predetermined nominal thickness is fed from the forming station 30 along the conveyor 32 in a machine direction 50 toward the cutting station 38. The cementitious board 25 has a cementitious core 53 interposed between a pair of cover sheets 54, 55. The cementitious core 53 is formed from an aqueous cementitious slurry. The cementitious board 25 has a pair of edges extending along the machine direction 50. The edges are disposed in lateral spaced relationship to each other along a cross-machine direction 51 which is perpendicular to the machine direction 50.

The wet end system 28 can include any suitable equipment adapted to mix and/or assemble the constituent materials forming the cementitious board 25. In embodiments, the wet end system 28 is configured as a gypsum wallboard wet end system.

In embodiments, the wet end system 28 includes a cementitious slurry mixing and dispensing system 72 having a slurry mixer 74 in fluid communication with a slurry dispensing system 76. The slurry mixer 74 is adapted to agitate water and a cementitious material (such as, calcined gypsum, for example) to form aqueous cementitious slurry. Both the water and the cementitious material can be supplied to the mixer 74 via one or more inlets as is known in the art. In embodiments, any other suitable slurry additive can be supplied to the mixer 74 as is known in the art of manufacturing cementitious products. Any suitable mixer (e.g., a pin mixer as is known in the art and commercially available from a variety of sources) can be used.

In use, water and a cementitious material, such as calcined gypsum, for example, can be agitated in the mixer 74 to form aqueous cementitious slurry. In some embodiments, water and calcined gypsum can be continuously added to the mixer 74 in a water-to-calcined gypsum ratio from about 0.5 to about 1.3, and in other embodiments of about 0.9 or less.

The slurry dispensing system 76 is in fluid communication with the slurry mixer 74 and is configured to dispense a main flow of cementitious slurry from the slurry mixer 74 upon a forming table extending between the cementitious slurry mixing and dispensing system 72 and the forming station 30. In embodiments, the slurry dispensing system 76 can include a suitable discharge conduit, as is known in the art. The discharge conduit can be made from any suitable material and can have different shapes. In some embodiments, the discharge conduit can comprise a flexible conduit. Cementitious slurry can be discharged from the slurry dispensing system 76 in an outlet flow direction substantially along the machine direction 50.

One or more flow-modifying elements can be associated with the discharge conduit and adapted to modify the flow of aqueous cementitious slurry from the slurry mixer 74 through the discharge conduit 76. The flow-modifying element(s) can be used to control an operating characteristic of the flow of aqueous cementitious slurry. Examples of suitable flow-modifying elements include volume restrictors, pressure reducers, constrictor valves, canisters, etc., including those described in U.S. Pat. Nos. 6,494,609; 6,874,930; 7,007,914; and 7,296,919, for example.

It is further contemplated that other discharge conduits, including other discharge conduits with different slurry distributors or boots, can be used in other embodiments of a cementitious slurry mixing and dispensing system 72. For example, in other embodiments, the discharge conduit 76 can include at its terminal end a slurry distributor similar to one of those shown and described in U.S. Patent Application Nos. 2012/0168527; 2012/0170403; 2013/0098268; 2013/0099027; 2013/0099418; 2013/0100759; 2013/0216717; 2013/0233880; and 2013/0308411, for example. In some of such embodiments, the discharge conduit 76 can include suitable components for splitting a main flow of cementitious slurry into two flows which are re-combined in the slurry distributor.

A first roll 78 of cover sheet material is configured to be selectively dispensed such that the first cover sheet 54 is dispensed from the first roll 74 upstream of the slurry dispensing system 76 and conveyed upon the forming table extending between the slurry mixer and dispensing system 72 and the forming station 30. A second roll 79 of cover sheet material is configured to be selectively dispensed such that the second cover sheet 55 is dispensed from the second roll 79 upon the forming table at a position between the slurry dispensing system 76 of the cementitious slurry mixing and dispensing system 72 and the forming station 30 over the first cover sheet 54 and the slurry dispensed from the slurry dispensing system 76. Gypsum board products are typically formed "face down" such that the first cover sheet 54 dispensed from the first roll 78 traveling over the forming table serves as the "face" cover sheet 54 of the finished cementitious board 25.

In embodiments, a foam injection system 80 can be arranged with at least one of the mixer 74 and the slurry dispensing system 76. The foam injection system 80 can include a foam source (e.g., such as a foam generation system configured as known in the art) and a foam supply conduit.

In embodiments, any suitable foam source can be used. Preferably, the aqueous foam is produced in a continuous manner in which a stream of a mix of foaming agent and water is directed to a foam generator, and a stream of the resultant aqueous foam leaves the generator and is directed to and mixed with the cementitious slurry. In embodiments, any suitable foaming agent can be used. Preferably, the aqueous foam is produced in a continuous manner in which a stream of the mix of foaming agent and water is directed to a foam generator, and a stream of the resultant aqueous foam leaves the generator and is directed to and mixed with the slurry. Some examples of suitable foaming agents are described in U.S. Pat. Nos. 5,683,635 and 5,643,510, for example.

The aqueous foam supply conduit can be in fluid communication with at least one of the slurry mixer 74 and the slurry dispensing system 76. An aqueous foam from a source can be added to the constituent materials through the foam supply conduit at any suitable location downstream of the mixer 74 in the slurry dispensing system 76 and/or in the mixer 74 itself to form a foamed cementitious slurry. In embodiments, the foam supply conduit is disposed downstream of the slurry mixer 74 and is associated with a main delivery trunk of the discharge conduit 76. In some embodiments, the aqueous foam supply conduit has a manifold-type arrangement for supplying foam to a plurality of foam injection ports defined within an injection ring or block disposed at a terminal end of the foam supply conduit and associated with the discharge conduit 76, as described in U.S. Pat. No. 6,874,930, for example. In embodiments, a flow-modifying element is disposed downstream of the foam injection body and the aqueous foam supply conduit relative to a flow direction of the flow of cementitious slurry from the mixer 74 through the discharge conduit 76.

In other embodiments, one or more foam supply conduits can be provided in fluid communication with the mixer 74. In yet other embodiments, the aqueous foam supply conduit(s) can be in fluid communication with the slurry mixer 74 alone. As will be appreciated by those skilled in the art, the means for introducing aqueous foam into the cementitious slurry in the cementitious slurry mixing and dispensing system 72, including its relative location in the system, can be varied and/or optimized to provide a uniform dispersion of aqueous foam in the cementitious slurry to produce board that is fit for its intended purpose.

In embodiments in which the cementitious slurry comprises gypsum slurry, one or both of the cover sheets 54, 55 can be pre-treated with a thin, relatively denser layer of gypsum slurry (relative to the gypsum slurry comprising the core), often referred to as a "skim coat" in the art, and/or hard edges, if desired. To that end, in embodiments, the mixer 74 can include a first auxiliary conduit that is adapted to deposit a stream of dense aqueous cementitious slurry that is relatively denser than the main flow of aqueous calcined gypsum slurry delivered to the discharge conduit 76 (i.e., a "face skim coat/hard edge stream").

In embodiments, a hard edge/face skim coat roller is disposed upstream of the slurry dispensing system 76 of the cementitious slurry mixing and dispensing system 72 and supported over the forming table such that the first cover sheet 54 being dispensed from the first roll 78 is disposed therebetween. The first auxiliary conduit can deposit the face skim coat/hard edge stream upon the first cover sheet 54 being dispensed from the first roll 78 upstream of the skim coat roller which is adapted to apply a skim coat layer to the moving first cover sheet 54 and to define hard edges at the periphery of the moving first cover sheet 54 by virtue of the width of the roller being less than the width of the moving first cover sheet 54 as is known in the art. Hard edges can be formed from the same dense slurry that forms the thin dense layer by directing portions of the dense slurry around the ends of the roller used to apply the dense layer to the first cover sheet 54.

In some embodiments, a back skim coat roller is disposed over a support element such that the second cover sheet 55 being dispensed from the second roll 79 is disposed therebetween. The mixer 74 can also include a second auxiliary conduit adapted to deposit a stream of dense aqueous calcined gypsum slurry that is relatively denser than the main flow of aqueous calcined gypsum slurry delivered to the discharge conduit 76 (i.e., a "back skim coat stream"). The second auxiliary conduit can deposit the back skim coat stream upon the moving second cover sheet 55 upstream (in the direction of movement of the second cover sheet 55) of the back skim coat roller that is adapted to apply a skim coat layer to the second cover sheet 55 being dispensed from the second roll 79 as is known in the art.

In other embodiments, separate auxiliary conduits can be connected to the mixer 74 to deliver one or more separate edge streams to the moving cover sheet. Other suitable equipment (such as auxiliary mixers) can be provided in the auxiliary conduits to help make the slurry therein denser, such as by mechanically breaking up foam in the slurry and/or by chemically breaking up the foam through use of a suitable de-foaming agent inserted into the auxiliary conduit(s) through a suitable inlet.

The skim coat rollers, the forming table, and the support element can all comprise equipment suitable for their respective intended purposes as is known in the art. The wet end system 28 can be equipped with other suitable equipment as is known in the art.

In use, the first cover sheet 54 is dispensed from the first roll 74 and moves along the machine direction 50. The cementitious slurry is discharged from the discharge conduit 76 upon the moving first cover sheet 54. The face skim coat/hard edge stream can be deposited from the mixer 74 at a point upstream of where the cementitious slurry is discharged from the discharge conduit 76 upon the moving first cover sheet 54 relative to the direction of movement of the first cover sheet 54 in the machine direction 50. A back skim coat stream (a layer of denser slurry relative to the main flow of cementitious slurry being discharged from the discharge conduit 86) can be applied to the second cover sheet 55 being dispensed from the second roll 79. The back skim coat stream can be deposited from the mixer 74 at a point upstream of the back skim coat roller relative to the direction of movement of the moving second cover sheet 55. In embodiments, aqueous foam or other agents can be added to the slurry comprising the face skim coat and/or back skim coat to reduce its density, but at a density that is greater than the foamed slurry dispensed from the discharge conduit.

The moving second cover sheet 55 can be placed upon the slurry deposited upon the advancing first cover sheet 54 to form a sandwiched wallboard preform that is fed to the forming station 30 to shape the preform to a desired thickness.

The forming station 30 is configured to form the cementitious board 25 such that the cementitious board 25 is within a predetermined thickness range. The forming station 30 can comprise any equipment suitable for its intended purpose as is known in the art. For example, in embodiments, the forming station can include a pair of forming plates or rolls in spaced relationship to each other along a normal axis 52 that is substantially perpendicular to the machine direction 50 and to the cross-machine direction 51. The cementitious board 25 passes through the vertically spaced-apart forming plates/rolls to determine the thickness of the cementitious board 25. Equipment can be provided that helps wrap the face cover sheet 54 around the sides of the sandwich to enclose the edges of the cementitious board 25, including applying an adhesive to secure the face cover sheet 54 to the back cover sheet 55.

The conveyor 32 is configured to convey the cementitious board 25 along the machine direction 50 away from the forming station 30. The conveyor 32 can be configured such that the edges of the cementitious board 25 extend in substantially parallel relationship with the machine direction 50. In embodiments, the conveyor 32 is configured such that it has a length, measured along the machine direction 50, sufficient to allow the cementitious slurry constituting the cementitious core 53 to adequately set before reaching the cutting station 38 such that the cementitious board 25 can be cut cleanly.

The conveyor 32 can comprise any equipment suitable for its intended purpose as is known in the art. In the illustrated embodiment, the conveyor 32 includes a plurality of support members 85 that define a support surface 102. In the illustrated embodiment, the support members 85 of the conveyor 32 comprise rollers that are journaled for rotation. In embodiments, at least a portion of the conveyor 32 can be equipped with a forming belt in overlying relationship to the rollers to help support the cementitious board spanning between the rollers and to help ensure a smooth surface for the face cover sheet 54.

The slurry set measurement system 34 is configured to measure a set characteristic of the aqueous cementitious slurry forming the core 53 of the cementitious board 25. In embodiments, the slurry set measurement system 34 is configured to be an automated test instrument to provide a measurement of a set characteristic (e.g., hardness, compression strength, and/or percent hydration) of the aqueous cementitious slurry of the cementitious board 25 during its production. The illustrated slurry set measurement system 34 is disposed downstream of the forming station 30 along the machine direction 50 and is disposed between the forming station 30 and the cutting station 38.

In embodiments, the slurry set measurement system 34 can comprise any suitable device configured to generate resistance force data by compressively engaging the cementitious board 25 in a controlled, automated manner at a designated location along the machine direction 50. A specially programmed processor can be used to correlate the resistance force data to a set characteristic possessed by the cementitious board 25 at that point in the production process. Referring to FIG. 1, in embodiments, the slurry set measurement system 34 can include a compression assembly 100, a height measuring device 102, a controller 104, a processor 108, a non-transitory computer readable medium 109 bearing a slurry set measurement application, and a display device 110.

The illustrated compression assembly 100 includes a compression member 120, an actuator assembly 122, and a force gauge 124. The compression member 120 is disposed over the conveyor 32 at a measurement position 125 which is in downstream relationship to the forming station 30 along the machine direction 50. The actuator assembly 122 is configured to selectively move the compression member 120 over a range of travel along the normal axis 52 between a stowed position (see, e.g., FIG. 3) and an engaged position (see, e.g., FIG. 1). The engaged position is configured to place the compression member 120 in contacting relationship with the cementitious board 25 supported by the conveyor 32 such that the compression member 120 exerts pressure against the cementitious board 25.

The force gauge 124 is associated with the compression member 120 to measure a resistance force against the compression member 120 along the normal axis 52 in response to the compression member 120 being in contacting relationship with the cementitious board 25. The force gauge 124 is configured to generate a force signal indicative of the resistance force.

The processor 108 is in communication with the force gauge 124 to receive the force signal therefrom. The processor 108 is programmed with the slurry set measurement application stored on the non-transitory computer readable medium 109 and is in operable arrangement with the display device 110. The slurry set measurement application can be configured to display, via the display device 110, a value for a set characteristic of the aqueous cementitious slurry forming the core 53 of the cementitious board 25. The value can be correlated to the force signal generated by the force gauge 124.

In embodiments, the measurement position 125 of the compression member 120 can be located at a variety of locations along the machine direction 50 downstream of the forming station 30. In embodiments, the measurement position 125 of the compression member 120 is located sufficiently downstream of the forming station 30 along the machine direction 50 such that the hydration reaction of the aqueous cementitious slurry forming the core 53 of the cementitious board 25 is at least halfway completed by the time that portion of the cementitious board 25 reaches the measurement location 125.

In embodiments, the compression member 120 can be substantially aligned with a support member (such as the conveyor roller 85', e.g.) along the machine direction 50. The support member 85' can help support the cementitious board 25 to facilitate the compression of the board 25 by the compression member 120 and to help prevent the compression member 120 from damaging the cementitious board 25 (e.g., cracking or tearing the cementitious board 25) to the extent that a process interruption would occur.

In the illustrated embodiment, the compression member 120 is in the form of a roller. The actuator assembly 122 is arranged with the roller 120 such that the roller 120 is rotatable about a rotation axis 128 with respect to the actuator assembly 122 (see also, detail view from FIG. 1). The rotation axis 128 can be substantially parallel to the cross-machine direction 51.

In the illustrated embodiment, the slurry set measurement system 34 includes a compression member mounting assembly 130 for rotatably supporting the compression member 120. The compression member mounting assembly 130 includes a mounting bracket 132, a pin 134, and a bearing 135. The roller 120 is journaled to the mounting bracket 132 for rotation about the rotation axis 128 via the pin 134, which defines the rotation axis 128. The bearing 135 is provided to allow the mounting bracket 132 is to be rotatable about the normal axis 52 with respect to the actuator assembly 122.

Figure 2:
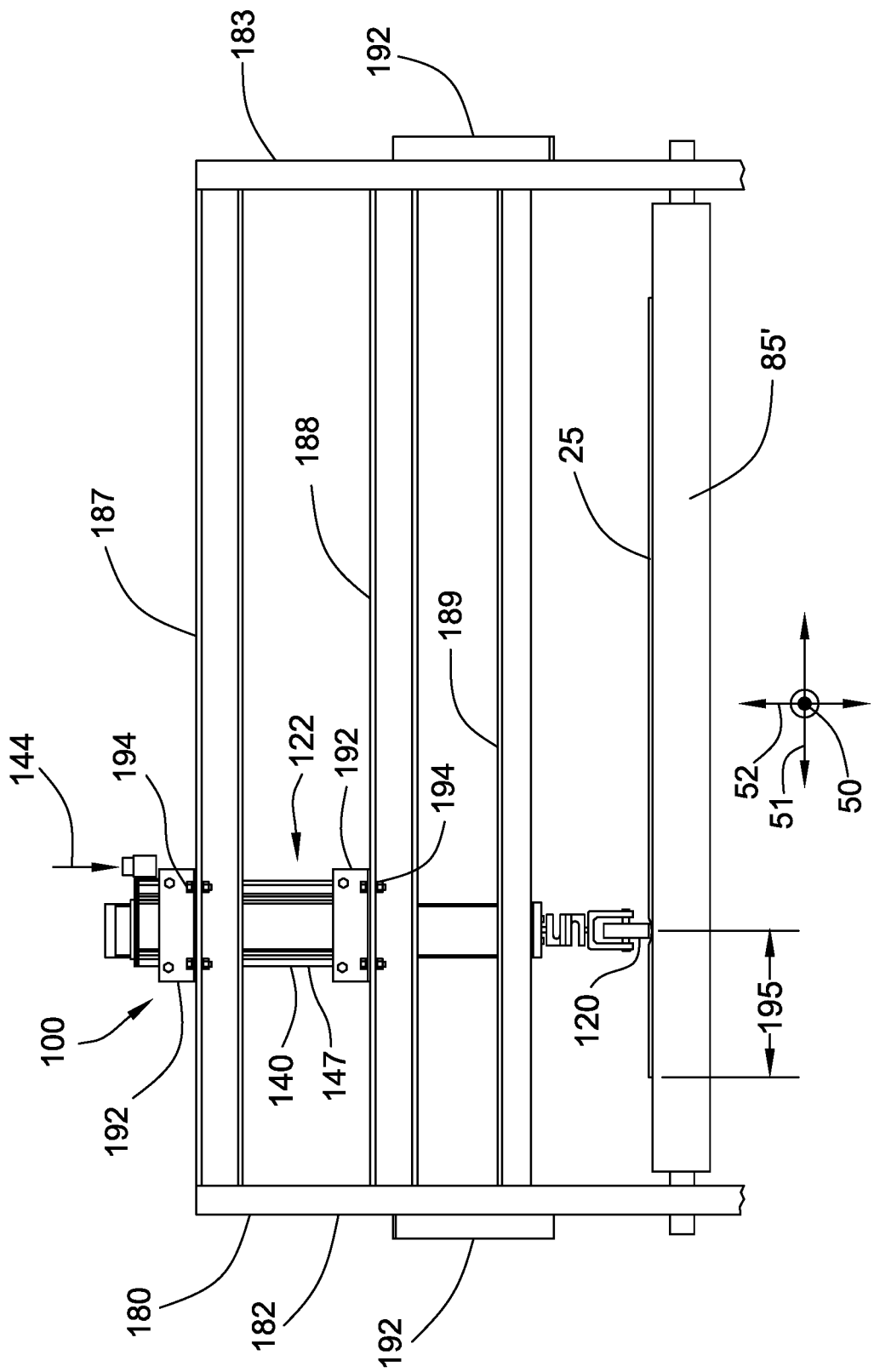
FIG. 2 is a fragmentary, end elevational view of the system for measuring set in the aqueous cementitious slurry of FIG. 1, illustrating a compression member in the form of a roller disposed in an engaged position.

In embodiments, the roller 120 can be in the form of a wheel with a thickness (along the cross-machine direction 51) that is less than its radius (see, e.g., FIG. 2). In other embodiments, the roller 120 can be in the form a cylindrical sleeve that has a length (along the cross-machine direction 51) that is greater than its radius.

In other embodiments, the compression member 120 can have any other suitable form. For example, in embodiments, the compression member 120 can be in the form of a body having a convex, curved contacting surface or can be in the form of a spherical bearing.

Referring to FIG. 1, the actuator assembly 122 can be configured to operate, in response to receiving a command signal from the controller 104, to selectively place the compression member 120 in engaging contact with the cementitious board 25 to measure a set characteristic of the cementitious board 25. In the illustrated embodiment, the actuator assembly 122 includes a linear actuator 140 and a linear actuator power source 144. In embodiments, the linear actuator 140 and the linear actuator power source 144 can comprise any suitable linear actuator equipment suitable for selectively moving the compression member 120 over a range of travel between a stowed position (see FIG. 3) and an engaged position (see, e.g., FIG. 1) and to deliver a sufficient compressive force to compress the cementitious board 25 a predetermined amount. For example, in embodiments, the actuator assembly 122 is configured to apply a compressive force of at least 200 lb-f.

Referring to FIG. 1, the illustrated linear actuator 140 comprises an integrated linear thruster having a body 147 and a slider shaft 149. The shaft 149 is reciprocally movable along the normal axis 52 with respect to the body 147. In the illustrated embodiment, the force gauge 124 is connected to the shaft 149, and the compression member mounting assembly 130 depends from the force gauge 124. The roller 120 is rotatably supported by the compression member mounting assembly 130.

The linear actuator power source 144 is configured to selectively operate the linear actuator 140 such that the linear actuator 140 moves the compression member 120 over the range of travel between the stowed position (see FIG. 3) and the engaged position (see, e.g., FIG. 1). The linear actuator power source 144 is in operable arrangement with the controller 104.

In embodiments, the linear actuator 140 can be configured to move the compression member 120 over a range of travel between the stowed position and the engaged position in a controlled manner. For example, in embodiments, the linear actuator 140 can be equipped with an encoder to help move the compression member 120 to a designated location along the normal axis 52. In embodiments, the linear actuator 140 can selectively move the shaft 149 relative to the body 147 in a compressing direction 150 such that the compression member 120 compresses the cementitious board 25 by a predetermined compression distance 152 (e.g., $\frac{1}{16}^{th}$ of an inch) for a variable range of cementitious board thicknesses.

In embodiments, reference height data generated by the reference height measuring device 102 can be used to determined the thickness of the particular board 25 and to calculate the particular engaged position for that thickness such that the compression distance 152 remains substantially uniform from measurement to measurement, and accommodating cementitious board of varying thicknesses. In embodiments, the controller 104 can receive position data for the engaged position from the processor 108, which can be programmed to calculate the location of the engaged position to achieve a uniform compression distance 152 using any of a variety of techniques, such as by using the known product formulation or by using data from the reference height measuring device 102 to determine the location along the normal axis 52 of the top surface (defined by the back cover sheet 55 in the case of gypsum wallboard, e.g.) of the cementitious board 25.

The force gauge 124 can be configured to transmit the resistance force data it obtains to the processor 108, which is configured to use the resistance force data to determine a set characteristic for the cementitious board 25 as the board 25 is being produced in a continuous manner. In embodiments, the force gauge 124 can comprise any suitable device configured to measure the resistance force generated by the cementitious board 25 in response to being compressed by the compression member 120.

In the illustrated embodiment, the force gauge 124 is interposed between the actuator assembly 122 and the compression member 120. The illustrated force gauge 124 comprises a compression type strain gauge load cell that is attached to the slider shaft 149 with a measurement bridge. In embodiments, the force gauge 124 can have any suitable measurement range (e.g., capable of measuring compression forces up to approximately 200 pounds).

The reference height measuring device 102 can be configured to generate board reference height data corresponding to a reference height of a portion of the cementitious board 25 as the cementitious board 25 is conveyed past the reference height measuring device 102 at a reference position 155. In embodiments, the reference position 155 can be disposed downstream of the forming station 30 along the machine direction 50. In embodiments, the reference position 155 is disposed between the forming station 30 and the measurement position 125 of the compression member 120 along the machine direction 50. In embodiments, the reference position 155 is located over a support member (such as the conveyor roller 85", for example). In embodiments, the reference position 155 is located over a support member 85" the defines a support surface that is substantially aligned along the normal axis 52 with a support surface 85' that underlies the compression member 120. In the illustrated embodiment, the reference position 155 is located along the machine direction 50 so that it is substantially aligned with the conveyor roller 85" along the machine direction 50. In other embodiments, the reference position 155 can be positioned at a different location along the machine direction 50 (such as, e.g., at the measurement position 125).

The processor 108 is in operable arrangement with the reference height measuring device 102 to receive the board reference height data therefrom. The slurry set measurement program can includes a height analysis module configured to set the engaged position based upon the corresponding board reference height data.

The height analysis module can be configured to determine the engaged position so that the engaged position is set at the predetermined compression distance 152 below the reference height of the cementitious board 25. The compression distance can be measured along the normal axis 52 between the reference height and the engaged position.

In the illustrated embodiment, the reference height measuring device 150 comprises a laser distance gauge. The reference height distance gauge 150 is suspended over the conveyor 32 along the normal axis 52 at a base height 170. The board reference height data includes a reference distance 172 between the base height 170 and the portion 155 of the cementitious board 25 as the cementitious board 25 is conveyed past the reference height distance gauge 102 at the reference position 155. The height analysis module can be configured to determine the engaged position based upon the reference distance 172 and a predetermined value for the compression distance 152.

In embodiments, the reference height measuring device 102 can be configured to obtain height data for a particular portion of the cementitious board 25 as it moves along the machine direction 50. The cementitious board 25 can be conveyed by the conveyor 32 past the reference height measuring device 102 such that reference height data corresponding to a given portion 155 of the cementitious board 25 can be acquired by the reference height measuring device 102 and transmitted to the board measurement processor 108. The reference height measuring device 102 can be configured to transmit the height data to the processor 108 which can be configured to determine an engaged position for the compression member 120 that corresponds to the predetermined compression distance 152 for compressing the cementitious board 25 a uniform amount from measurement to measurement on a sequential basis using the relative height data from the reference height measuring device 102.

The illustrated slurry set measurement system 34 is configured to generate board reference height data corresponding to the portion of the cementitious board 25 as the cementitious board 25 is conveyed from the forming station 30 along the machine direction 50 past the reference position 155 of the reference height measuring device 102 toward the cutting station 38. In embodiments, the processor 108 is in operable communication with a line speed sensor and/or the controller 104 in order to receive a line speed signal therefrom. The slurry set measurement program can be configured to use the line speed signal to help compare the reference height 172 and the resistance force data of the same portion of the cementitious board 25 rather than different portions of the cementitious board 25 that are simultaneously passing through the reference position 155 and the measurement position 125 along the machine direction 50 at any given time during the continuous operation of the board line.

In embodiments, the reference height data and the resistance force data can both include collection time data, as well. The slurry set measurement program can use the line speed signal in conjunction with a measurement device separation distance 175, measured along the machine direction 50 between the reference position 155 and the measurement position 125, and the time data to match the reference height and the resistance force data for a given portion 155 of the cementitious board 25.

Referring to FIG. 1, the controller 104 is in operable arrangement with the compression assembly 100, the reference height measuring device 102, and the processor 108. In embodiments, the controller 104 is configured to selectively operate the compression assembly 100 to generate resistance force data corresponding to a portion of the cementitious board 25 as the cementitious board 25 passes by the compression assembly 100 along the machine direction 50.

The controller 104 is in operable arrangement with the linear actuator power source. The controller 104 can be configured to selectively operate the linear actuator power source 144 to move the compression member 120 of the slurry set measurement system 34 from the stowed position to the engaged position in response to at least one of a command signal being received by the controller 104 and a predetermined period of time having elapsed.

In embodiments, the controller 104 can be configured to move the compression member 120 in the compressing direction 150 from the stowed position to the engaged position until: (i) the compression member 120 compresses the portion of the cementitious board 25 by the predetermined compression distance 152 along the normal axis 52, or (ii) the resistance force measured by the force gauge 124 is equal to or greater than a predetermined resistance force threshold, whichever occurs first. The controller 104 can be configured to move the compression member 120 in a retraction direction 180, in opposing direction to the compressing direction 150 along the normal axis, back to the stowed position once the set measurement is obtained.

In embodiments, the controller 104 can include a user input and/or interface device having one or more user actuated mechanisms (e.g., one or more push buttons, slide bars, rotatable knobs, a keyboard, and a mouse) adapted to generate one or more user actuated input control signals. In embodiments, the controller 104 can be configured to include one or more other user-activated mechanisms to provide various other control functions for the slurry set measurement system, as will be appreciated by one skilled in the art. The controller 104 can include a display device adapted to display a graphical user interface. The graphical user interface can be configured to function as both a user input device and a display device in embodiments. In embodiments, the display device can comprise a touch screen device adapted to receive input signals from a user touching different parts of the display screen. In embodiments, the controller 104 can be in the form of a smart phone, a tablet, a personal digital assistant (e.g., a wireless, mobile device), a laptop computer, a desktop computer, or other type of device. In embodiments, the controller 104 and the processor 108 can comprise the same device or set of equipment.

In the illustrated embodiment, the processor 108 is in operable arrangement with the controller 104 to facilitate the control and the operation of the slurry set measurement system 34. The processor 108 can be configured to receive input signals from the controller 104, to send input control signals to the controller 104, and/or to send output information to the controller 104. The processor 108 is in operable arrangement with the force gauge 124 to receive the resistance force data therefrom and with the reference height measuring device 102 to receive the board reference height data therefrom. The processor 108 is in operable arrangement with the non-transitory computer-readable medium 109 to execute the slurry set measurement program contained thereon. The processor 108 is in operable arrangement with the display device 110 to selectively display output information from the slurry set measurement program and/or to receive input information from a graphical user interface displayed by the display device 110.

In embodiments, the board measurement processor 108 is configured to display the resistance force data received from the compression assembly 100 in the display device 110. The resistance force data can also be stored in a data storage device operably arranged with the board measurement processor 108, and/or to correlate the resistance force data with a board set characteristic, such as, the degree to which the cementitious slurry constituting the cementitious core 53 of a given portion of the cementitious board has set (e.g. expressed as a percent value of hydration).

In embodiments, the board measurement processor 108 can comprise any suitable computing device, such as, a microprocessor, a mainframe computer, a digital signal processor, a portable computing device, a personal organizer, a device controller, a logic device (e.g., a programmable logic device configured to perform processing functions), a digital signal processing (DSP) device, or a computational engine within an appliance. In embodiments, the board measurement processor 108 also includes one or more additional input devices (e.g., a keyboard and a mouse).

The board measurement processor 108 can have one or more memory devices associated therewith to store data and information. The one or more memory devices can include any suitable type, including volatile and non-volatile memory devices, such as RAM (Random Access Memory), ROM (Read-Only Memory), EEPROM (Electrically-Erasable Programmable Read-Only Memory), flash memory, etc. In one embodiment, the board measurement processor 108 is adapted to execute programming stored upon a non-transitory computer readable medium to perform various methods, processes, and modes of operations in a manner following principles of the present disclosure.

In embodiments, the non-transitory computer readable medium 109 can contain a slurry set measurement program that is configured to implement an embodiment of a method for manufacturing cementitious board according to principles of the present disclosure. In embodiments, the slurry set measurement program includes a graphical user interface that can be displayed by the display device 110. The graphical user interface can be used to facilitate the inputting of commands and data by a user to the slurry set measurement program and to display outputs generated by the slurry set measurement program.

The slurry set measurement program can be stored upon any suitable computer-readable storage medium. For example, in embodiments, a slurry set measurement program following principles of the present disclosure can be stored upon a hard drive, floppy disk, CD-ROM drive, tape drive, zip drive, flash drive, optical storage device, magnetic storage device, and the like.

In embodiments, the slurry set measurement application is configured to use the force signal transmitted from the force gauge 124 to determine a set characteristic of the aqueous cementitious slurry forming the core 53 of the cementitious board 25. In embodiments, the resistance force data (or a correlated set characteristic) can be displayed by the slurry set measurement program via the graphical user interface in the display device 110. In embodiments, an operator can set a predetermined tolerance range for the resistance force (or a correlated set characteristic), and the slurry set measurement program can be configured to operate an alarm if the resistance force (or a correlated set characteristic) falls outside of the tolerance range. In embodiments, the alarm can be any suitable alarm including an audible signal and/or a warning message displayed via the graphical user interface on the display device 110.

In embodiments, the slurry set measurement program is configured to correlate the resistance force data it receives from the compression assembly 100 (via the force signal) to a numerical value of percent hydration of the aqueous cementitious slurry forming the core 53 of a particular portion of the cementitious board 25. In embodiments, the slurry set measurement program is configured to determine the value of percent hydration of the aqueous cementitious slurry forming the core 53 of the particular portion of the cementitious board 25 using a database of values of percent hydration correlated to a set of resistance force values. In other embodiments, the slurry set measurement program is configured to determine the value of percent hydration of the aqueous cementitious slurry of the particular portion of the cementitious board using a conversion formula including the resistance force value as a part of the formula.

In embodiments, the board measurement processor 108 is in operable communication with a data storage device which includes at least one database containing board characteristic data. In embodiments, the slurry set measurement program can be configured to map the resistance force data generated from the compression assembly 100 with the board characteristic data to correlate a particular resistance force value with a value for a set characteristic of the cementitious board 25.

For example, in embodiments, the data storage device includes a database of values of percent hydration that were determined using historical temperature rise data for a given product type. In embodiments, the slurry set measurement program can be configured to map the resistance data generated from the slurry set measurement system 34 with the values of percent hydration that were determined using historical temperature rise data to correlate a particular resistance force value with a value for percent hydration of the cementitious slurry forming the core 53 of the cementitious board 25 when it was at the measurement position 125 at which the compression member 120 is located along the machine axis 50.

In embodiments, the database of historical temperature rise data can include temperature rise data organized by product type and by nominal product thickness. In embodiments, the temperature rise data can be acquired by any suitable technique known to one skilled in the art. For example, in embodiments, the temperature rise data can be acquired in periodic fashion using any one of a variety of known techniques to one skilled in the art.

For example, in embodiments, the temperature rise setting time is determined in accordance with CSA A82.20M 1977 Physical Testing of Gypsum Plasters, Section 5.3, herein incorporated by reference. Since hydration of calcined gypsum is an exothermic reaction, the temperature rise in the slurry from the initial mixing temperature is indicative of the degree of set in the cementitious slurry.

In other embodiments, the rate of hydration is evaluated on the basis of the "Time to 50% Hydration." Because the hydration of calcined gypsum to set gypsum is an exothermic process, the Time to 50% Hydration can be calculated by determining the midpoint of the temperature increase caused by the hydration and then measuring the amount of time required to generate the temperature rise, as is known to those skilled in the art. In some embodiments, the Time to 50% Hydration can be determined by pouring a cementitious slurry into a standardized cup, which is then placed into an insulated container made from closed-cell extruded polystyrene foam (e.g., Styrofoam®) to reduce heat transfer with the environment. A temperature probe is placed into the middle of the slurry, and the temperature is recorded every five seconds. Since the setting reaction is exothermic, the extent of the reaction can be measured by the temperature rise. The time to 50% hydration is determined to be the time to reach the temperature halfway between the minimum and maximum temperatures recorded during the test.

In still other embodiments, the temperature rise setting time is determined in accordance with ASTM C472-99, which is entitled, "Standard Test Methods for Physical Testing of Gypsum, Gypsum Plasters and Gypsum Concrete." ASTM C472 includes a procedure which uses a Vicat apparatus to test the level of setting of gypsum. The ASTM C472 procedure can be similarly used for any other cementitious slurry suitable for use with principles described herein. The Vicat apparatus uses a needle to penetrate cementitious material, the degree to which the needle penetrates the setting slurry correlates to the hydration percentage of the slurry. According to ASTM C472, the setting time is complete when the needle no longer penetrates to the bottom of the material.

In yet other embodiments, a continuous, real-time slurry temperature rise monitoring system can be provided along the machine direction 50 between the mixer 74 and the kiln, for example. In embodiments, any suitable slurry temperature rise monitoring system known to those skilled in the art can be used, such as, those commercially-available from Raytek Corp. of Santa Cruz, Calif., including the system marketed under the model name TRS100, for instance.

In embodiments, the continuous, real-time slurry temperature rise monitoring system includes a series of infrared sensors disposed in spaced relationship to each other along the board line. Each infrared sensor can be configured to detect infrared radiant energy (heat) and convert the detected thermal energy values into an electronic signal, which is then processed to produce thermal data for the cementitious board 25 as it travels along the machine direction. In embodiments, an infrared sensor is disposed at or near the measurement position 125. In embodiments, at least one infrared sensor is disposed between the mixer 84 and the forming station 30 along the machine direction 50 and at least one infrared sensor is disposed between the forming station 30 and the cutting station 38. In embodiments, at least one infrared sensor is disposed between the cutting station 38 and a dryer (e.g., a kiln) disposed downstream from the cutting station 38 along the machine direction 50.

The processor 108 can execute a thermal processing program stored on a non-transitory computer-readable medium to generate a time/temperature graph representing the rise/set temperatures from the infrared sensors of the slurry temperature rise monitoring system. The thermal processing program can also be configured to store time/temperature data representing the rise/set temperatures of cementitious slurry for a given product type and nominal thickness in the data storage device for use by the slurry set measurement program. In embodiments, the slurry temperature rise monitoring system can include sensors for monitoring the board line speed, ambient air temperature at each infrared sensor, the board formulation recipe, and predefined process parameters, for example.

Figure 3:
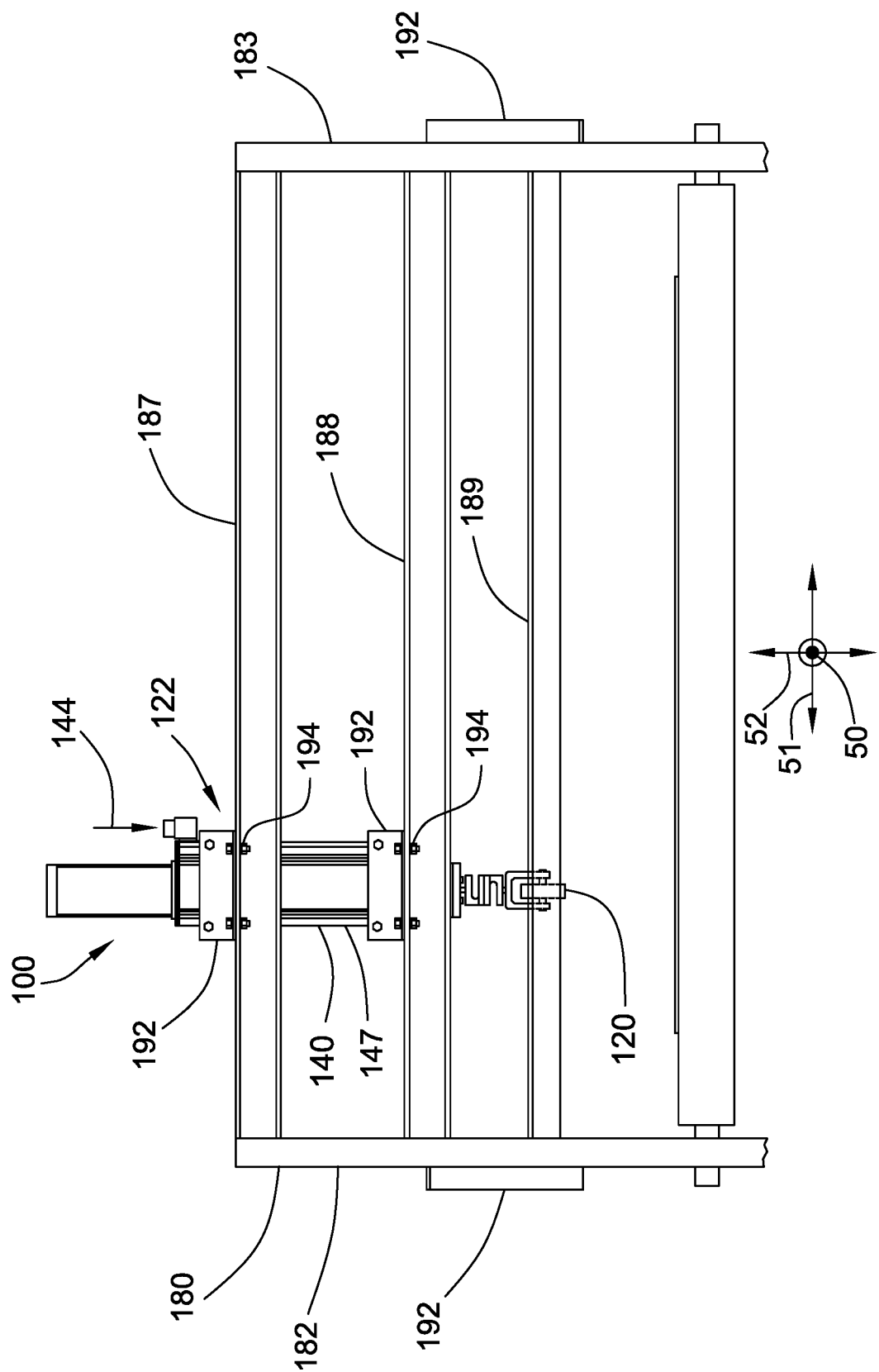
FIG. 3 is a view as in FIG. 2, but illustrating the compression roller disposed in a stowed position.
Figure 4:
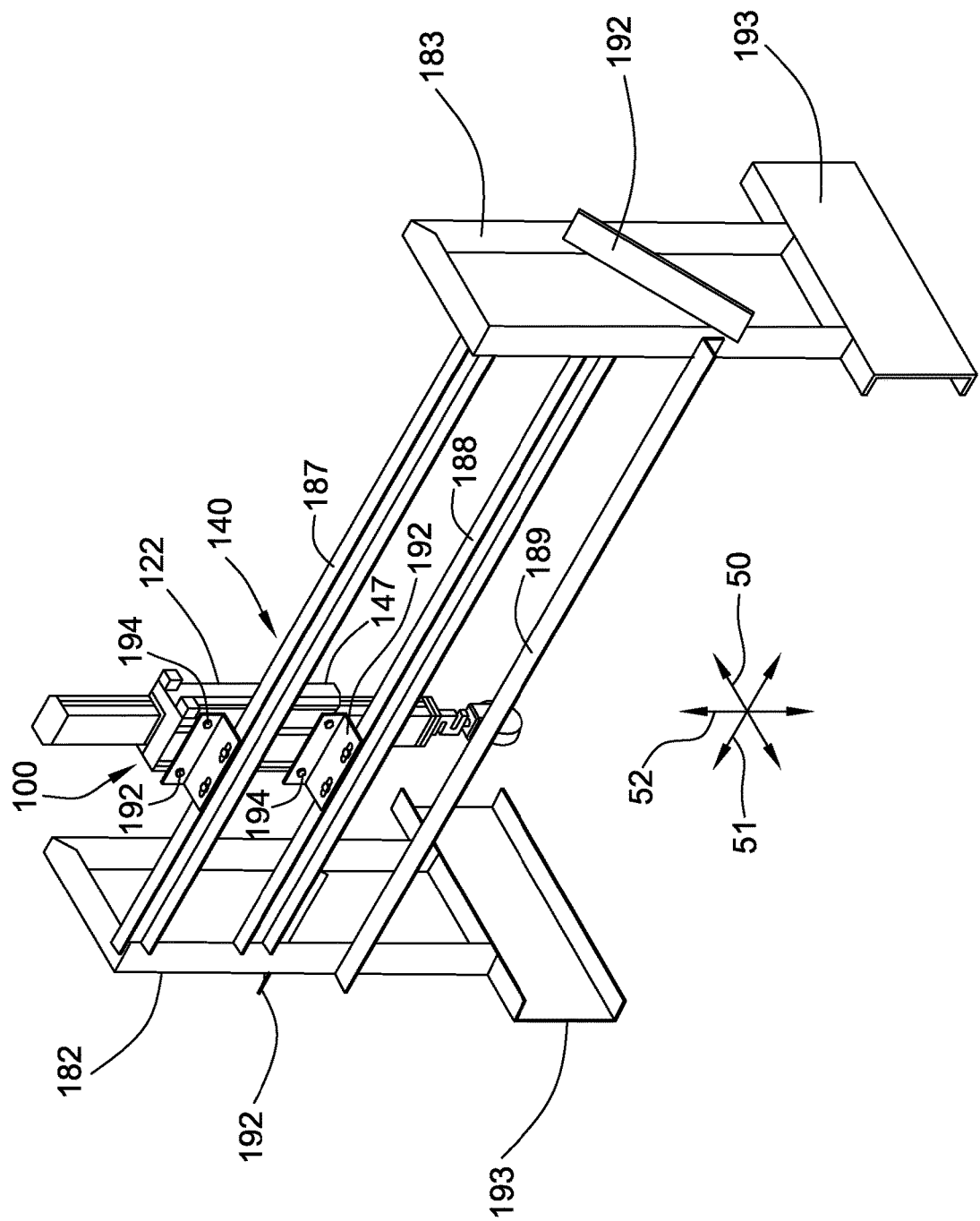
FIG. 4 is a perspective view of the system for measuring set in the aqueous cementitious slurry of FIG. 1.

Referring to FIG. 2-4, in embodiments, the slurry set measurement system 34 can include a support frame 180 configured to support the actuator assembly 122 over the conveyor 32. The illustrated support frame 180 includes pair of uprights 182, 183 extending along the normal axis 52, a pair of support rails 187, 188 extending along the cross-machine direction 51 over the conveyor 32, and a cross-machine connecting member 189 also extending along the cross-machine direction 51.

In the illustrated embodiment, each upright 182, 183 includes a cross-brace 192 and a conveyor mounting element 193. The conveyor mounting element 193 can be configured to facilitate the connection of the respective upright 182, 183 to the conveyor 32. The support rails 187, 188 are in spaced relationship to each other along the normal axis 152 and extend along the cross-machine direction 51 between the uprights 182, 183. The support rails 187, 188 can be configured to support the compression assembly 100 in place over the conveyor 32. The cross-machine connecting member 189 can be provided to help laterally support the uprights 182, 183.

In embodiments, the actuator assembly 122 is connected to at least one of the support rail 187, 188. In the illustrated embodiment, the actuator assembly 122 is mounted to both of the support rails 187, 188. The linear actuator 140 can be mounted to the support frame 180. In particular, in the illustrated embodiment, the body 147 of the linear actuator 140 is secured to the support rails 187, 188 via a plurality of mounting feet brackets 192 and fasteners 194. The mounting feet brackets 192 can be variably positioned along the support rails 187, 188 to change the position of the compression member 120 relative to the cementitious board 25.

For example, in the illustrated embodiment as shown in FIG. 2, the compression member 120 is located a cross-machine measurement distance 195 from one of the edges of the cementitious board 25. In the illustrate embodiments, the cross-machine distance 195 is less than half the width of the cementitious board 25, as measured along the cross-machine direction 51. In embodiments, the cross-machine measurement distance 195 can be varied (such as, e.g., being located along the cross-machine midpoint of the cementitious board 25, or being located closer or further from the edge of the cementitious board 25).

Referring to FIG. 1, the cutting station 38 is disposed downstream of the forming station 30 along the machine axis 50. The cutting station 38 is arranged with respect to the conveyor 32 such that the conveyor 32 carries the cementitious board 25 past the cutting station 38. The cutting station 38 can include a knife configured to periodically cut the cementitious board 25 along the cross-machine direction 51 to define a series of board segments as the cementitious board 25 moves along the machine direction 50 past the cutting station 38. In embodiments, the knife can be a rotary knife as is generally known to those skilled in the art.

In embodiments, the slurry set measurement system 34 is located upstream of the cutting station 38 along the machine direction 50. In the illustrated embodiment, the slurry set measurement system 34 is disposed along the machine direction 50 between the forming station 30 and the cutting station 38.

In embodiments, the controller 104 can be configured to control the operation of the rotary knife of the cutting station 38. In embodiments, the controller 104 can adjust the rotational speed of the rotary knife based upon the line speed of the board line (as detected by a suitable sensor, for example) to produce board segments of substantially the same length under different line speed conditions.

In embodiments, the system 20 for manufacturing a cementitious board 25 can include other components and stations. For example, in embodiments, the system 20 can include a transfer system, including a board inverter; a kiln; and a bundler and taping station, all downstream of the cutting station 38.

In embodiments of a method of manufacturing a cementitious board following principles of the present disclosure, a system for measuring set in aqueous cementitious slurry according to principles of the present disclosure is used to determine the degree to which cementitious slurry within the cementitious board is set in an on-line manner during the continuous manufacture of the cementitious board. For example, in embodiments, to measure a set characteristic of the aqueous cementitious slurry of the cementitious board (such as, e.g., hardness or suitability to cut), the actuator assembly can be operated to lower the compression member into the cementitious board by a predetermined compression distance (e.g., up to $\frac{1}{16}^{th}$ of an inch). In embodiments where the compression member comprises a roller, the roller rotates about its rotation axis in response to the relative movement of the cementitious board with respect to the roller along the machine direction. The force gauge transmits a force signal to the processor, which in turn, analyzes the resistance force indicated by the force signal. The processor can continue to signal the controller to continue to lower the compression member in the compressing direction along the normal axis until a predetermined threshold force value is reached, or the compression member has reached a predetermined compression distance (e.g., $\frac{1}{16}^{th}$ of an inch), whichever occurs first. The processor can be used to display in a display device through a graphical user interface of the slurry set measurement application whether the board is suitable to cut if the required threshold force value occurred, or not suitable to cut if the predetermined compression limit was reached but the measured resistance force did not reach a minimum value for the resistance force. In embodiments, the slurry set measurement program can be used to correlate the measured resistance force with a numerical value of percent hydration of the aqueous cementitious slurry of one or more particular portions of the cementitious board. Testing can be periodically repeated until the cementitious board is determined to be sufficiently set at the testing location. Thereafter, testing can be performed at another time interval (such as a longer time interval) to periodically to confirm that the cementitious board is sufficiently set such that the that hardness is still satisfactory.

Figure 5:
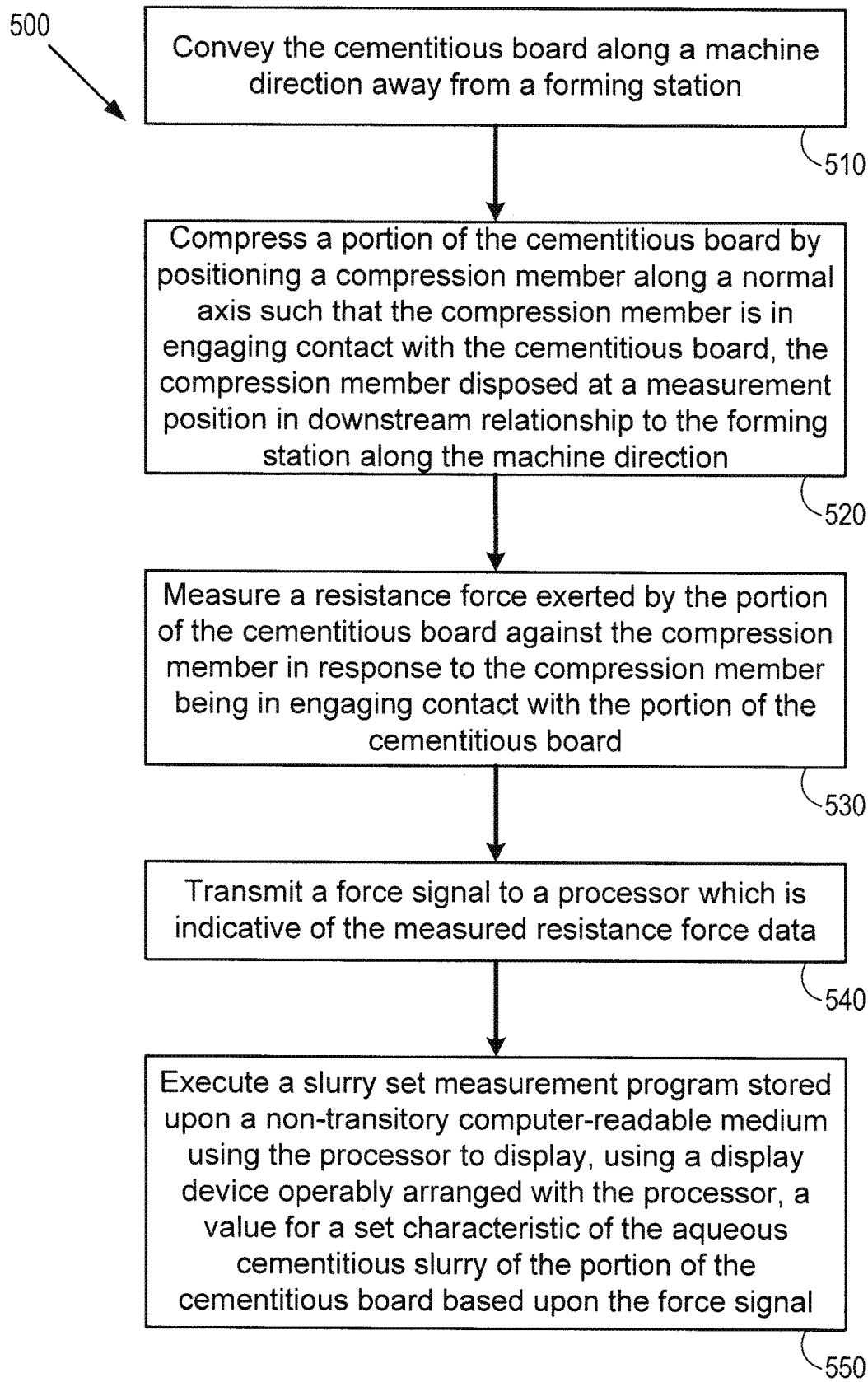
FIG. 5 is a flowchart illustrating steps of an embodiment of method of manufacturing a cementitious board following principles of the present disclosure.

Referring to FIG. 5, steps of an embodiment of a method 500 of manufacturing a cementitious board following principles of the present disclosure are shown. In embodiments, a method of manufacturing a cementitious board following principles of the present disclosure can be used with any embodiment of a system for measuring set in aqueous cementitious slurry according to principles discussed herein.

The illustrated method 500 of manufacturing a cementitious board includes conveying the cementitious board along a machine direction away from a forming station (step 510). The cementitious board has a cementitious core interposed between a pair of cover sheets. The cementitious core comprises an aqueous cementitious slurry. The cementitious board extends along the machine direction and along a cross-machine direction, which is perpendicular to the machine direction.

A portion of the cementitious board is compressed by positioning a compression member along a normal axis such that the compression member is in engaging contact with the portion of the cementitious board (step 520). The normal axis is substantially perpendicular to the machine direction and to the cross-machine direction. The compression member is disposed at a measurement position in downstream relationship to the forming station along the machine direction.

In embodiments, compressing the portion of the cementitious board includes moving the compression member along the normal axis in a compressing direction to increasingly compress the cementitious board. In embodiments, the compression member is moved in the compressing direction until: (i) the compression member compresses the portion of the cementitious board by a predetermined compression distance along the normal axis, or (ii) the resistance force is equal to or greater than a predetermined resistance force threshold, whichever occurs first.

In embodiments, the compression member comprises a roller. The roller is rotatable about a rotation axis in response to the cementitious board being conveyed along the machine direction when the roller is in sufficient engaging contact therewith.

A resistance force, which is exerted by the portion of the cementitious board against the compression member in response to the compression member being in engaging contact with the portion of the cementitious board, is measured (step 530). The force signal is transmitted to a processor (step 540). The force signal is indicative of the measured resistance force.

A slurry set measurement program stored upon a non-transitory computer-readable medium is executed using the processor to display a value for a set characteristic of the aqueous cementitious slurry of the portion of the cementitious board based upon the force signal (step 550). The value is displayed through a graphical user interface using a display device operably arranged with the processor. In embodiments, the slurry set measurement application is configured to determine a set characteristic of the aqueous cementitious slurry of the portion of the cementitious board based upon the force signal. In embodiments, the slurry set measurement application is configured to correlate the force signal for the portion of the cementitious board to a numerical value of percent hydration of the aqueous cementitious slurry of the portion of the cementitious board.

In embodiments of a method of manufacturing a cementitious board following principles of the present disclosure, executing the slurry set measurement program stored upon the non-transitory computer-readable medium using the processor includes displaying, through a graphical user interface, the value of percent hydration of the aqueous cementitious slurry of the particular portion of the cementitious board in a display device. In embodiments, an operator may use the measured resistance force directly as a numerical value relating to a set characteristic which can be displayed through the graphical user interface in the display device. In embodiments, an operator may use the compression distance attained when the measured resistance force reaches a predetermined threshold value as a numerical value relating to a set characteristic which can be displayed through the graphical user interface in the display device. In other embodiments, the slurry set measurement program is configured to correlate the measured resistance force and/or the compression distance attained when the measured resistance force reaches a predetermined threshold value with corresponding values for the percent hydration of the aqueous cementitious slurry of the particular portion of the cementitious board. In embodiments, the slurry set measurement program can be in operable relationship with a data storage device configured to receive resistance force data, compression distance data, and set characteristic data based upon the resistance force data and/or compression distance data on a continuous basis from the processor.

In embodiments of a method of manufacturing a cementitious board following principles of the present disclosure, a reference height of the portion of the cementitious board is measured along the normal axis. Reference height data are transmitted to the processor. The reference height data are indicative of the reference height of the portion of the cementitious board. The slurry set measurement program stored upon the non-transitory computer-readable medium is executed using the processor to determine an engaged position for the compression member based upon the reference height data so that the compression member compresses the portion of the cementitious board by the compression distance along the normal axis. The compression member is moved along the normal axis in a compressing direction toward the engaged position.

In embodiments of a method of manufacturing a cementitious board following principles of the present disclosure, the compression member is moved into a stowed position such that the compression member is placed in non-contacting relationship with the cementitious board. The compression member can be periodically reciprocally moved between the stowed position and the engaged position for a series of portions of the cementitious board. The compression member is moved in a compressing direction along the normal axis toward the engaged position until: (i) the compression member compresses the portion of the cementitious board by the compression distance along the normal axis, or (ii) the resistance force is equal to or greater than a predetermined resistance force threshold, whichever occurs first. The set characteristic of the aqueous cementitious slurry of the series of portions of the cementitious board can be respectively determined based upon the respective force signal generated for each measurement. In embodiments, the interval between measurements can be varied.

In embodiments, the compression member can be placed in a stored position (which is even further from the conveyor than the stowed position) at start up to provide more clearance space above the cementitious board during start up. For example, in embodiments, the actuator assembly can be rotatably secured to the support from such that the compression assembly can be pivoted away from the conveyor.

In embodiments of a method of manufacturing a cementitious board following principles of the present disclosure, the cementitious board is periodically cut to define a series of board segments as the cementitious board moves along the machine direction past a cutting station. The cutting station is disposed downstream of the forming station along the machine direction. The compression member is interposed between the forming station and the cutting station along the machine direction.

All references cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A system for manufacturing a cementitious board, the cementitious board having a cementitious core interposed between a pair of cover sheets, the cementitious core formed from an aqueous cementitious slurry, the system comprising:
   a forming station, the forming station configured to form the cementitious board such that the cementitious board is within a predetermined thickness range;
   a conveyor, the conveyor configured to convey the cementitious board along a machine direction away from the forming station, the conveyor extending along the machine direction and a cross-machine direction, the cross-machine direction being perpendicular to the machine direction;
   a slurry set measurement system, the slurry set measurement system configured to measure a set characteristic of the aqueous cementitious slurry of the cementitious board, the slurry set measurement system including a compression member, an actuator assembly, and a force gauge, wherein:
      the compression member is disposed over the conveyor at a measurement position, the measurement position in downstream relationship to the forming station along the machine direction,
      the actuator assembly is configured to selectively move the compression member over a range of travel along a normal axis between a stowed position and an engaged position, the normal axis being substantially perpendicular to the machine direction and to the cross-machine direction, and the engaged position being configured to place the compression member in contacting relationship with the cementitious board supported by the conveyor such that the compression member exerts pressure against the cementitious board, and
      the force gauge is associated with the compression member such that the force gauge is configured to measure a resistance force against the compression member along the normal axis in response to the compression member being in contacting relationship with the cementitious board, the force gauge configured to generate a force signal indicative of the resistance force.

2. The system for manufacturing according to claim 1, wherein the slurry set measurement system includes a processor, a non-transitory computer readable medium bearing a slurry set measurement application, and a display device in operable arrangement with the processor, the processor being in communication with the force gauge to receive the force signal therefrom, the processor programmed with the slurry set measurement application, the slurry set measurement application being configured to display via the display device a value for a set characteristic of the aqueous cementitious slurry of the cementitious board, the value being correlated to the force signal.

3. The system for manufacturing according to claim 2, wherein the slurry set measurement system includes a reference height measuring device, the reference height measuring device disposed downstream of the forming station at a reference position, the reference height measuring device being configured to generate board reference height data corresponding to a reference height of a portion of the cementitious board as the cementitious board is conveyed past the reference height measuring device at the reference position, wherein the processor is in operable arrangement with the reference height measuring device to receive the board reference height data therefrom, wherein the slurry set measurement program includes a height analysis module configured to set the engaged position based upon the corresponding board reference height data.

4. The system for manufacturing according to claim 3, wherein the height analysis module is configured to determine the engaged position so that the engaged position is a predetermined compression distance below the reference height of the cementitious board, the compression distance being measured along the normal axis between the reference height and the engaged position.

5. The system for manufacturing according to claim 3, wherein the reference height measuring device comprises a laser distance gauge disposed over the conveyor along the normal axis at a base height, wherein the board reference height data includes a reference distance between the base height and the portion of the cementitious board as the cementitious board is conveyed past the reference height distance gauge at the reference position.

6. The system for manufacturing according to claim 5, wherein the height analysis module is configured to determine the engaged position based upon the reference distance and a predetermined value for the compression distance.

7. The system for manufacturing according to claim 1, wherein the slurry set measurement system includes a processor and a non-transitory computer readable medium bearing a slurry set measurement application, the processor being in communication with the force gauge to receive the force signal therefrom, the processor programmed with the slurry set measurement application, the slurry set measurement application being configured to use the force signal to determine a set characteristic of the aqueous cementitious slurry of the cementitious board.

8. The system for manufacturing according to claim 7, wherein the slurry set measurement application is configured to correlate the force signal for a particular portion of the cementitious board to a numerical value of percent hydration of the aqueous cementitious slurry of the particular portion of the cementitious board.

9. The system for manufacturing according to claim 1, wherein the force gauge is interposed between the actuator assembly and the compression member.

10. The system for manufacturing according to claim 9, wherein the compression member comprises a roller, the actuator assembly being arranged with the roller such that the roller is rotatable about a rotation axis with respect to the actuator assembly, the rotation axis being substantially parallel to the cross-machine direction.

11. The system for manufacturing according to claim 10, wherein the slurry set measurement system includes a mounting bracket, the roller being journaled to the mounting bracket for rotation about the rotation axis, and wherein the mounting bracket is connected to the force gauge such that the mounting bracket is rotatable about the normal axis with respect to the actuator assembly.

12. The system for manufacturing according to claim 1, wherein the slurry set measurement system includes a support frame, the support frame configured to support the actuator assembly over the conveyor.

13. The system for manufacturing according to claim 12, wherein the support frame includes pair of uprights extending along the normal axis and a support rail extending along the cross-machine direction over the conveyor, the actuator assembly connected to the support rail.

14. The system for manufacturing according to claim 12, wherein the actuator assembly includes a linear actuator and a linear actuator power source, the linear actuator being mounted to the support frame, the linear actuator power source being configured to selectively operate the linear actuator such that the linear actuator moves the compression member over the range of travel.

15. The system for manufacturing according to claim 14, wherein the slurry set measurement system includes a controller, the controller being in operable arrangement with the linear actuator power source, the controller configured to selectively operate the linear actuator power source to move the compression member of the slurry set measurement system from the stowed position to the engaged position in response to at least one of a command signal being received by the controller and a predetermined period of time having elapsed.

16. The system for manufacturing according to claim 1, further comprising:
a cutting station, the cutting station disposed downstream of the forming station along the machine direction, the cutting station arranged with respect to the conveyor such that the conveyor carries the cementitious board past the cutting station, the cutting station including a knife configured to periodically cut the cementitious board along the cross-machine direction to define a series of board segments as the cementitious board moves along the machine direction past the cutting station, the slurry set measurement system being disposed along the machine direction between the forming station and the cutting station.

17. A method of manufacturing a cementitious board, the method comprising:
conveying the cementitious board along a machine direction away from a forming station, the cementitious board having a cementitious core interposed between a pair of cover sheets, the cementitious core comprising an aqueous cementitious slurry, the cementitious board extending along the machine direction and along a cross-machine direction, the cross-machine direction perpendicular to the machine direction;
compressing a portion of the cementitious board by positioning a compression member along a normal axis such that the compression member is in engaging contact with the portion of the cementitious board, the normal axis being substantially perpendicular to the machine direction and to the cross-machine direction, the compression member disposed at a measurement position in downstream relationship to the forming station along the machine direction;
measuring a resistance force exerted by the portion of the cementitious board against the compression member in response to the compression member being in engaging contact with the portion of the cementitious board;
transmitting a force signal to a processor, the force signal indicative of the measured resistance force;
executing a slurry set measurement program stored upon a non-transitory computer-readable medium using the processor to display a value for a set characteristic of the aqueous cementitious slurry of the portion of the cementitious board based upon the force signal, the value being displayed through a graphical user interface using a display device operably arranged with the processor.

18. The method of manufacturing according to claim 17, wherein the slurry set measurement application correlates the force signal for the portion of the cementitious board to a numerical value of percent hydration of the aqueous cementitious slurry of the portion of the cementitious board.

19. The method of manufacturing according to claim 17, wherein compressing the portion of the cementitious board includes moving the compression member along the normal axis in a compressing direction to increasingly compress the cementitious board.

20. The method of manufacturing according to claim 19, wherein the compression member is moved in the compressing direction until: (i) the compression member compresses the portion of the cementitious board by a predetermined compression distance along the normal axis, or (ii) the resistance force is equal to or greater than a predetermined resistance force threshold, whichever occurs first.

21. The method of manufacturing according to claim 19, wherein the compression member comprises a roller, the roller rotating about a rotation axis in response to the cementitious board being conveyed along the machine direction.

22. The method of manufacturing according to claim 17, further comprising:
measuring a reference height of the portion of the cementitious board, the reference height measured along the normal axis;
transmitting reference height data to the processor, the reference height data indicative of the reference height of the portion of the cementitious board;
executing the slurry set measurement program stored upon the non-transitory computer-readable medium using the processor to determine an engaged position for the compression member based upon the reference height data so that the compression member compresses the portion of the cementitious board by the compression distance along the normal axis;
moving the compression member along the normal axis in a compressing direction toward the engaged position.

23. The method of manufacturing according to claim 17, further comprising:
moving the compression member into a stowed position such that the compression member is placed in non-contacting relationship with the cementitious board.

24. The method of manufacturing according to claim 23, further comprising:
periodically reciprocally moving the compression member between the stowed position and the engaged position for a series of portions of the cementitious board, the compression member being moved in a compressing direction along the normal axis toward the engaged position until: (i) the compression member compresses the portion of the cementitious board by the compression distance along the normal axis, or (ii) the resistance force is equal to or greater than a predetermined resistance force threshold, whichever occurs first;
respectively determining the set characteristic of the aqueous cementitious slurry of the series of portions of the cementitious board based upon the respective force signal.

25. The method of manufacturing according to claim 17, further comprising:
periodically cutting the cementitious board to define a series of board segments as the cementitious board moves along the machine direction past a cutting station, the cutting station disposed downstream of the forming station along the machine direction, and the compression member interposed between the forming station and the cutting station along the machine direction.

* * * * *